US 6,587,711 B1

(12) United States Patent
Alfano et al.

(10) Patent No.: US 6,587,711 B1
(45) Date of Patent: Jul. 1, 2003

(54) SPECTRAL POLARIZING TOMOGRAPHIC DERMATOSCOPE

(75) Inventors: Robert R. Alfano, Bronx, NY (US); Yury Budansky, Oakland, NJ (US); Jingcheng Luo, New York, NY (US)

(73) Assignee: The Research Foundation of Cuny, New York, NY (US)

( * ) Notice: Subject to any disclaimer, the term of this patent is extended or adjusted under 35 U.S.C. 154(b) by 0 days.

(21) Appl. No.: 09/550,094

(22) Filed: Apr. 14, 2000

Related U.S. Application Data
(60) Provisional application No. 60/144,975, filed on Jul. 22, 1999.

(51) Int. Cl.[7] .................................................. A61B 6/00

(52) U.S. Cl. ........................ 600/476; 600/410; 600/425

(58) Field of Search ................................ 600/476, 410, 600/425

(56) References Cited

U.S. PATENT DOCUMENTS

| | | | |
|---|---|---|---|
| 3,910,701 A | * 10/1975 | Henderson et al. | 356/39 |
| 5,719,399 A | 2/1998 | Alfano et al. | |
| 5,825,502 A | 10/1998 | Mayer | |
| 5,847,394 A | 12/1998 | Alfano et al. | |
| 5,851,181 A | * 12/1998 | Talmor | 600/407 |
| 5,929,443 A | 7/1999 | Alfano et al. | |
| 6,010,450 A | 1/2000 | Perkins | |
| 6,032,071 A | * 2/2000 | Binder | 600/476 |
| 6,070,092 A | * 5/2000 | Kazama et al. | 600/310 |
| 6,104,945 A | * 8/2000 | Modell et al. | 600/473 |
| 6,217,512 B1 | * 4/2001 | Salo et al. | 600/160 |
| 6,236,881 B1 | * 5/2001 | Zahler et al. | 600/476 |
| 6,332,092 B1 | * 12/2001 | Deckert et al. | 600/476 |

OTHER PUBLICATIONS

Seidenari et al., "Digital videomicroscopy and image analysis with automatic classification for detection of thin melanomas," Melanoma Research, 9:163–71 (1999).

* cited by examiner

Primary Examiner—Marvin M. Lateef
Assistant Examiner—Devaang Shah
(74) Attorney, Agent, or Firm—Kriegsman & Kriegsman

(57) ABSTRACT

An apparatus for use in examining an object, such as skin, mucosa and cervical tissues for the purpose of detecting cancer and precancerous conditions therein. In one embodiment, the apparatus includes a gun-shaped housing having a handle portion and a barrel portion. The front end of the barrel portion is open, and a glass cover is mounted therein. Red, green, blue, and white LED's are disposed within the handle portion of the housing and are electrically connected to a battery also disposed within the handle portion of the housing. A manually-operable switch for controlling actuation of each of the four LED's is accessible on the handle portion of the housing. An optical fiber is disposed inside the housing and is used to transmit light from the four LED's through a first polarizer disposed in the barrel portion of the housing and then through the glass cover to illuminate a desired object. Reflected light from the object entering the housing through the glass cover is passed through a second polarizer, which is adjustably mounted in the barrel portion of the housing and which is preferably oriented to pass depolarized light emitted from an illuminated object, and is then imaged by optics onto a CCD detector. The optics may include a lens that is disposed within the barrel portion and is adjustably spaced relative to the CCD detector. The detector is coupled to a wireless transmitter mounted in the housing, the transmitter transmitting the output from the detector to a remotely located wireless receiver. The wireless receiver is coupled to a computer, which then processes the output from the detector. The processed output is then displayed on a display. The display may be remotely situated for remote expert diagnosis.

25 Claims, 5 Drawing Sheets

SPECTRAL POLARIZING TOMOGRAPHIC DERMATOSCOPE

CROSS-REFERENCE TO RELATED APPLICATIONS

The present application claims the benefit under 35 U.S.C. §119(e) of U.S. Provisional Patent Application Ser. No. 60/144,975, filed Jul. 22, 1999, the disclosure of which is incorporated herein by reference.

BACKGROUND OF THE INVENTION

The present invention relates generally to the examination of skin, mucosa and cervical tissues for the purpose of detecting cancer and precancerous conditions and relates more particularly to a novel apparatus for use in performing examinations of the aforementioned types.

Cutaneous melanoma is a disease of increasing clinical and economic importance, both in the United States and abroad. For this reason, the early detection of cancerous and precancerous lesions is particularly important at preventing the progression of the disease. To highlight the importance of early detection, data from the National Cancer Database of the United States indicate that 37% of those patients who have been diagnosed with melanoma have advanced primary lesions that can spread to regional lymph nodes or beyond—often with dire consequences.

Despite the fact that approximately 1 in 87 Americans will be diagnosed with melanoma during his/her lifetime, the public, on balance, lacks the foresight and the ability to perform satisfactory self-examinations. In addition, the examination of skin by primary care, non-dermatologist physicians is uncommon, and such non-dermatologist physicians are poorly prepared to recognize and to diagnose melanomas. Notwithstanding the above, the benefits associated with skin examinations are becoming increasingly more apparently as an increase in skin examinations has been correlated with a reduction in the incidence of melanoma, as well as with a reduction in the development of advanced disease among melanoma patients.

Skin examinations typically involve visually inspecting the skin for lesions and evaluating any detected lesions according to well-defined criteria, such as the ABCD rule wherein A=asymmetry, B=border irregularity, C=color variability and D=diameter >6 mm. Potential melanomas detected according to the foregoing technique are then typically biopsied in order to permit a final diagnosis.

The visual inspection of skin is typically performed with the unaided eye, with a hand-held magnifying glass or with the assistance of an instrument known as a dermatoscope. One problem associated with visually inspecting skin with the unaided eye or with a magnifyring glass is that much of the light used to illuminate the skin being examined is difflusely reflected by the outermost surface of the skin, thereby obfuiscating much of the subsurface structures of interest. Another problem associated with visually inspecting skin with the unaided eye or with a magnifying glass is that certain lesions are too small to be readily detected.

A dermatoscope is typically a hand-held device that is constructed to address both of the shortcomings identified above. A dermatoscope typically comprises an elongated, hollow housing having a pair of open ends, one of the ends being covered with a glass cover adapted to be pressed against the skin of a patient, the other end being adapted for viewing by an operator. A white light source (e.g., lamp) and illuminating optics are disposed within the housing for illuminating the skin sample, and magnifying optics are appropriately positioned within the housing for magnifying the illuminated skin sample for viewing by the operator.

Typically, in use, the operator applies mineral oil or organic chemical solvent (alcohol) the skin to be examined and then presses the glass cover of the dermatoscope against the solvent or oil-covered skin. The mineral oil or solvent substantially matches the index of refraction of the outermost layers of skin and, thereby, renders said outermost layers sufficiently translucent to permit observation of underlying skin structures. The magnifying optics of the dermatoscope permits observation of structures that would otherwise be too small to detect with the unaided eye or with a magnifying glass.

Although, as explained above, conventional dermatoscopes provide a measure of improvement over the unaided eye or a magnifying glass, conventional dermatoscopes still suffer from certain drawbacks. One such drawback is that the operator must bring his/her face down into proximity with the dermatoscope and, by extension, must bring his/her face down into proximity with the patient's skin. As can readily be appreciated, such an arrangement is not hygienic. Another such drawback is that no permanent record of the observation of the skin is taken as the skin is viewed directly by the operator. Also, no telemedicine information can be relayed for expert diagnosis and advice.

Accordingly, one type of modification that has been made to conventional dermatoscopes has been to include means for producing and recording a videoimage of the examined skin. An example of such a dermatoscope is disclosed in U.S. Pat. No. 5,825,502, inventor Mayer, which issued Oct. 20, 1998, and which is incorporated herein by reference. According to the aforementioned patent, there is disclosed a mobile device for close-up-photography or videorecording that is easily usable for the investigation of surface details of an object which is particularly large and soft, for example, human skin. When placed in contact with the surface of the object, then without further adjustments a sharp and greatly enlarged image is obtained. The device includes a distance-enforcing structure between the optical system and the object which in the object-side focal area ends with a vaulted surface. The vaulted surface is mechanically stiff and is shaped to compensate the image-plane curvature of the optical system by establishing a corresponding object-plane curvature. This compensation: enhances the sharpness of the image obtained for an object surface which is pressed against the vaulted surface and thus is positioned in the true object-side focal area of the optical system.

Another example of a dermatoscope that includes means for producing and recording a videoimage of examined skin is disclosed in U.S. Pat. No. 6,010,450, inventor Perkins, which issued Jan. 4, 2000, and which is incorporated herein by reference.

Another problem associated with the examination of skin, whether said skin is observed with the unaided eye or with the aid of a derniatoscope, is that the analysis of the observed image often requires the application of qualitative and/or poorly-defined criteria. Such criteria may be judged differently by different individuals, thereby, leading to a lack of uniformity in diagnosis among various observers. Accordingly, one approach to this problem has been to automate the analysis of the recorded images obtained using a dermatoscope. An example of the aforementioned approach is described by Seidenari et al. in "Digital videomicroscopy and image analysis with automatic classification for detection of thin melanomas," *Melanoma*

Research, 9:163–171 (999), the disclosure of which is incorporated herein by reference.

As can readily be appreciated, one disadvantage associated with the use of dermatoscopes of the types described above is that mineral oil, solvent or the like must be applied to the patient's skin in order to minimize diffuse reflection at the outermost layer of skin and, in so doing, to render the skin more transparent to white lamp light. One approach to this problem has been to have the dermatoscope use polarized lamp light to illuminate the skin under examination and to have the dermatoscope image the underlying structures of the illuminated skin using the perpendicular component of the reflected light. An example of this approach is disclosed in U.S. Pat. No. 6,032,071, inventor Binder, which issued Feb. 29, 2000, and which is incorporated herein by reference. According to the aforementioned patent, a device for optical examination of human skin and its pigmentation is described that comprises a cylindrical housing in which are arranged an optical observation device and a vertical illumination device. Where it faces the skin, the housing is delimited by a plate made of transparent plastics or glass, which is applied to a skin site to be examined without introducing an immersion fluid. Light polarization devices are situated between the illumination device and the transparent plate and between the transparent plate and the optical observation device, their degree of polarization being controlled or, optionally, their location being movable mechanically into or out of particular light beam paths.

Although dermatoscopes of the types described above have enabled significant advances in skin examination to take place, substantial room for improvement still exists.

Other patents and publications of interest include U.S. Pat. No. 5,719,399, inventors Alfano et al., issued Feb. 17, 1998; U.S: Pat. No. 5,847,394, inventors Alfano et al., issued Dec. 8, 1998; U.S. Pat. No. 5,929,443, inventors Alfano et al., issued Jul. 27, 1999; Gutkowicz-Krusin et al., *Skin Research and Technology*, 3:15–22 (1997); Robert Pini, *Biophotonic International*, pages 20–21 (September 1998); Kopf et al., *Skin Research Technology*, 3:1–7 (1997); Nachbar et al., *J. Am. Acad. Dermatol.*, 30(4):551–9 (1994); and Menzies et al., "A sensitivity and specificity analysis of the surface microscopy features of invasive melanoma," *Melanoma Res.*, 6(1):55–62 (1996), all of which are incorporated herein by reference.

SUMMARY OF THE INVENTION

It is an object of the present invention to provide a new apparatus suitable for use in examining skin, mucosa and cervical tissues for the purpose of detecting cancer and precancerous conditions therein.

It is another object of the present invention to provide an apparatus as described above that overcomes at least some of the problems associated with existing devices for performing such examinations.

Therefore, according to one aspect of the invention, there is provided an apparatus suitable for use in examining skin, mucosa and cervical tissues for the purpose of detecting cancer and precancerous conditions therein, said apparatus comprising (a) first illuminating means for illuminating an object with polarized light of a first color; (b) second illuminating means for illuminating an object with polarized light of a second color, said second color being different from said first color; (c) a control coupled to each of said first illuminating means and said second illuminating means to permit selective actuation of said first illuminating means and said second illuminating means; (d) a light detector for outputting an electrical signal in response to light incident thereonto; (e) an adjustable polarizer positioned between said light detector and the illuminated object; (f) optics for imaging light emitted from the illuminated object onto said light detector; (g) a computer for processing the output from said light detector; (h) means for transmitting the output from said light detector to said computer; and (i) a display for displaying the results of said processing from said computer. The display may be located proximally relative to said computer and connected directly thereto or may be located remotely relative to said computer and connected to said computer, for example, via modem and a second computer.

In a preferred embodiment, the apparatus comprises a gun-shaped housing having a handle portion and a barrel portion. The front end of the barrel portion is open, and a glass cover is mounted therein. Red, green, blue, and white LED's are disposed within the handle portion of the housing and are electrically connected to a battery also disposed within the handle portion of the housing. A manually-operable switch for controlling actuation of each of the four LED's is accessible on the handle portion of the housing. An optical fiber is disposed inside the housing and is used to transmit light from the four LED's, through a first polarizer disposed in the barrel portion of the housing and then through the glass cover to illuminate a desired object. Reflected light from the object entering the housing through the glass cover is passed through a second polarizer, which is adjustably mounted in the barrel portion of the housing, and is then imaged by optics onto a CCD detector. The optics may include a lens that is disposed within the barrel portion and is adjustably spaced relative to the CCD detector. The detector is coupled to a wireless transmitter mounted in the housing, the transmitter transmitting the output from the detector to a remotely located wireless receiver. The wireless receiver is coupled to a computer, which then processes the output from the detector. The processed output is then displayed on a display or relayed by telemedicine to remote sites for diagnosis by experts.

Additional objects, features, aspects and advantages of the present invention will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute apart of this specification, illustrate preferred embodiments of the invention and, together with the description, serve to explain the principles of the invention. In the drawings wherein like reference numerals represent like parts.

DETAILED DESCRIPTION OF PREFERRED EMBODIMENTS

Figure 1:
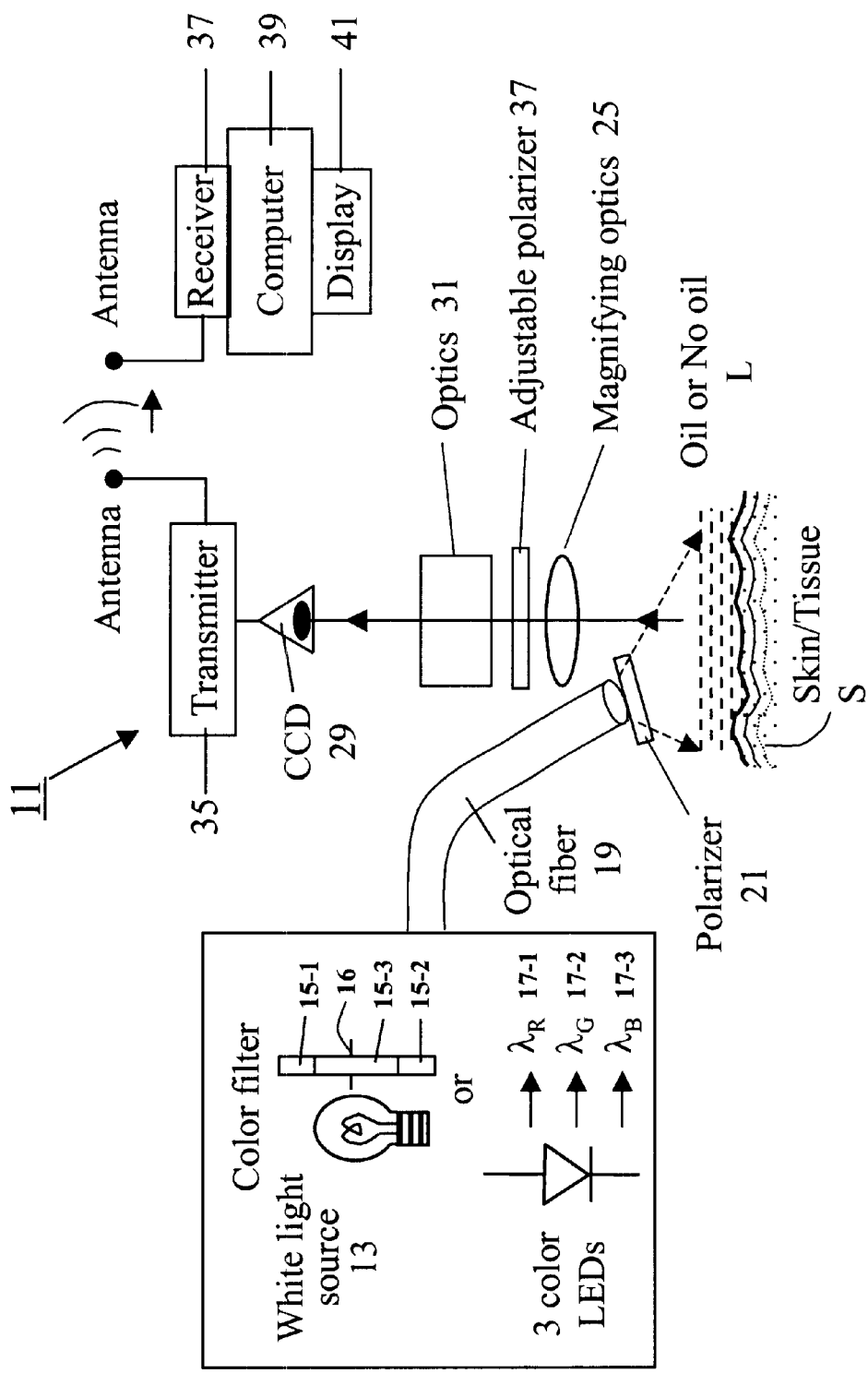
FIG. 1 is a schematic diagram of a first embodiment of an apparatus constructed according to the teachings of the present invention for use in examining objects.

Referring now to FIG. 1, there is shown a schematic diagram of a first embodiment of an apparatus constructed according to the teachings of the present invention for use in examining objects, said apparatus being represented generally by reference numeral 11. Apparatus 11 may be used, for example, to examine an object, such as skin, mucosa and cervical tissues for the purpose of detecting cancer and precancerous conditions therein or to examine a solid or structured object for the purpose of detecting defects therein.

Apparatus 11 comprises first illuminating means for illuminating an object with polarized light of a first color. In the present embodiment, said first illuminating means may comprise a white light source 13, such as a white light lamp emitting 2.5 mW and a filter 15-1 selective for light of a first color. Filter 15-1 may be, for example, a narrow band filter selective for substantially monochromatic red light or a wide band filter selective for somewhat less monochromatic red light. Alternatively, instead of the aforementioned combination of white light source 13 and filter 15-1, said first illuminating means may comprise a first light-emitting diode (LED) 17-1 of a first color, such as a red light-emitting diode emitting 0.4 mW at 630 nm. Said first illuminating means also comprises an optical fiber 19 for transmitting the light of said first color from the combination of white light source 13 and filter 15-1 or LED 17-1 to the object to be examined, said object in the present embodiment being shown to be a skin sample S which may or may not be treated with an index of refraction-matching oil L. Said first illuminating means further comprises a polarizer 21, which may be, for example, a linear polarizer, positioned at the output end of optical fiber 19 for polarizing the light used to illuminate skin sample S. The illuminated area is on the order of 3.8 $cm^2$.

Apparatus 11 also comprises second illuminating means for illuminating an object with light of a second color, said second color being different than said first color. In the present embodiment, said second illuminating means may comprise white light source 13 and a filter 15-2 selective for light of a second color. Filter 15-2 may, for example, be a narrow band filter selective for substantially monochromatic green light or a wide band filter selective for somewhat less monochromatic green light. Alternatively, instead of the aforementioned combination of white light source 13 and filter 15-2, said second illuminating means may comprise a second light-emitting diode 17-2 of a second color, such as a green LED emitting 0.36 mW at 526 nm. Said second illuminating means also comprises optical fiber 19 and polarizer 21, the output from the combination of white light source 13 and filter 15-2 or from LED 17-2 being inputted into optical fiber 19 and transmitted by optical fiber 19 through polarizer 21 and to skin sample S.

Apparatus 11 also comprises third illuminating means for illuminating an object with polarized light of a third color, said third color being different than said first and second colors. In the present embodiment, said third illuminating means may comprise white light source 13 and a filter 15-3 selective for light of a third color. (In the present embodiment, filters 15-1, 15-2 and 15-3 are rotatably mounted on a filter wheel 16.) Filter 15-3 may be, for example, a narrow band filter selective for substantially monochromatic blue light or a wide band filter selective for somewhat less monochromatic blue light. Alternatively, instead of the aforementioned combination of white light source 13 and filter 15-3, said third illuminating means may comprise a third light-emitting diode 17-3 of a third color, such as a blue LED emitting 0.3 mW at 472 nm. Said third illuminating means also comprises optical fiber 19 and polarizer 21, the output from the combination of white light source 13 and filter 15-3 or from LED 17-3 being inputted into optical fiber 19 and transmitted by optical fiber 19 through polarizer 21 and to skin sample S.

Although not shown, apparatus 11 also includes a control coupled to each of said first, second and third illuminating means to permit the selective actuation by an operator of said first, second and third illuminating means, either individually or in various combinations.

Apparatus 11 additionally includes magnifying optics 25 for magnifying the illuminated area of skin sample S, an adjustable polarizer/analyzer 27 positioned behind magnifying optics 25 for selecting a desired polarization component of the magnified light, a light detector 29 for detecting the selected polarization component, and imaging optics 31 positioned between adjustable polarizer 27 and light detector 29 for imaging the light passed by polarizer 27 onto light detector 29. Light detector 25 may be, for example, a black and white CCD detector or a color video camera.

Apparatus 11 further includes a radio frequency transmitter 35. Transmitter 35 is coupled to detector 25 and is used to convert the output from detector 25 into RF signals that are transmitted to a remotely positioned radio frequency receiver 37. Receiver 37, which converts RF signals into electrical signals, is coupled to a computer 39 and transmits the signals it receives thereto. Computer 39 processes the information corresponding to the light signals detected by detector 25 and transmits the results of said processing to a display 41, where the results of said processing are displayed. Display 41 may be located proximally relative to said computer and connected directly thereto, as shown in the present embodiment, or may be located remotely relative to said computer and connected to said computer, for example, via modem and a second computer.

Figure 2:
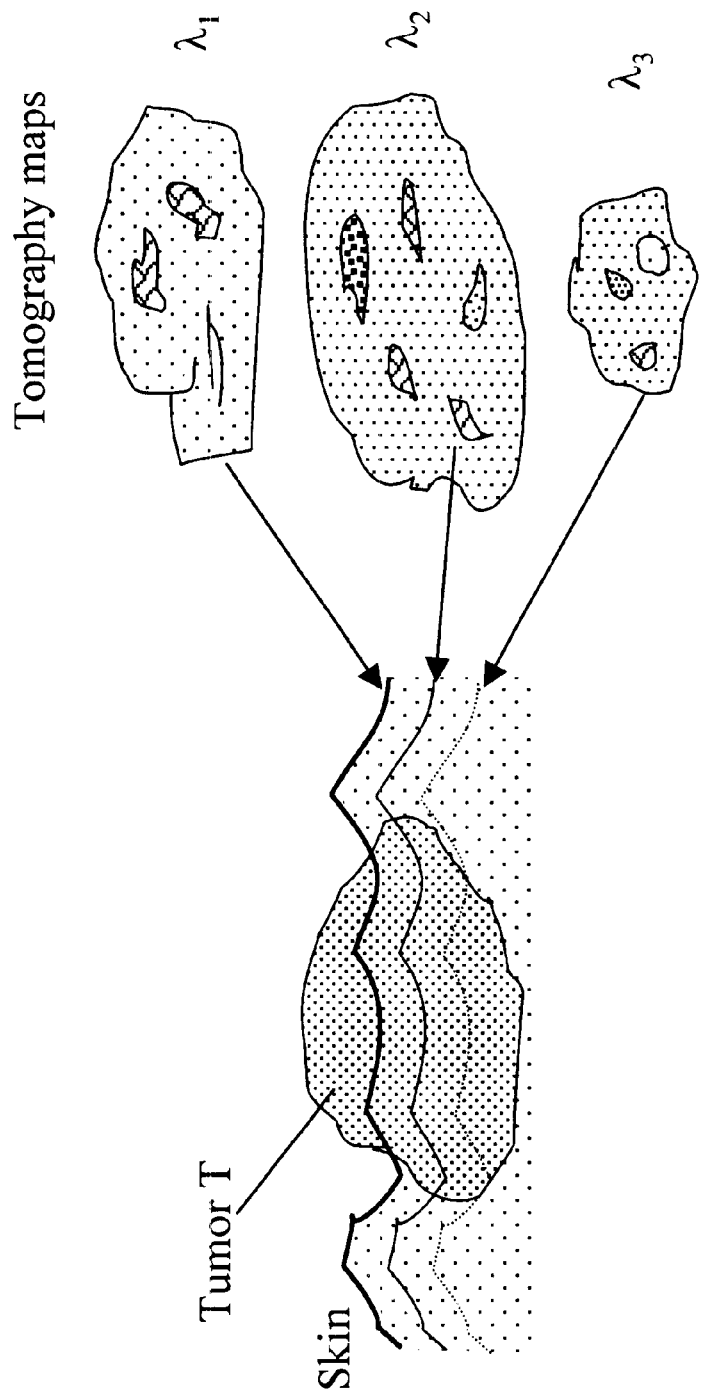
FIG. 2 is a schematic section view of a tumor embedded in the skin of a patient and various tomography maps of the tumor obtained at different wavelengths using the apparatus of FIG. 1.

Referring now to FIG. 2, there are shown a schematic section view of a tumor T embedded in the skin of a patient and three different images of tumor T obtained using apparatus 11. As can be seen, by illuminating the tumor with polarized light of three different colors and using the perpendicular polarization component of the backscattered light, one can obtain images of the tumor at three different depths thereof. Red light gives the deepest penetration (~2 mm) of tissue, followed by green light (~½ mm) and blue light (~¼ mm). Surface information of the skin sample can additionally be obtained by using the parallel polarization component of the backscattered light. These different images can jointly be used to form a tomographic map of the tumor and thus provide considerably more information than is typically provided using conventional dermatoscopes. These images can then be evaluated for the presence of malignancies or other precancerous conditions by trained personnel according to the aforementioned ABCD test or can be evaluated for the presence of malignancies or other precancerous conditions by computer 39 according to the ABCD test or based on other criteria discussed above or hereinafter described. The image can be combined to use color images to determine the presence of a blue veil for a cancer fingerprint. For example, monochromatic images of reflected light from lesions can be acquired at the three different wavelengths of the red, green and blue spectral regions. Using the image data, the Kubelka-Munk transformation can be applied to produce maps of the tissue absorption at the two or more wavelength bands (such as spectral zones of red, green and blue). These absorptions maps can be compared to both maps from normal skin tissue, and normal tissue regions within the images. The differences in absorption can be related to changes in melanin content, and other biochemical and structural changes which may indicate the presence of melanoma. For wavelengths in the 250 to 300 nm region, the DNA and protein content can be obtained, i.e., 265 nm for DNA and 280 nm for protein.

The Kubelka-Munk function, KMF $(x, y, \lambda) = (1-R)^2 / 2R$, can be plotted and mapped over the area (x,y) of a tissue (skin) from measuring reflectance $R(\lambda)$ at wavelength band $\lambda$ at (x,y) points. Differential map image of surface for perpendicular intensity $I\perp(x,y,\lambda)$, reflectance $R(x,y,\lambda)$ or $KMF(x,y,\lambda)$ such as $I\perp(x,y,\lambda_1) - I\perp(x,,y,\lambda_2)$. For red image subtracted from green light image will give depth information of objects far below the surface. For blue image subtracted from the green will give information on objects at a lesser depth just below the surface.

Figure 3:
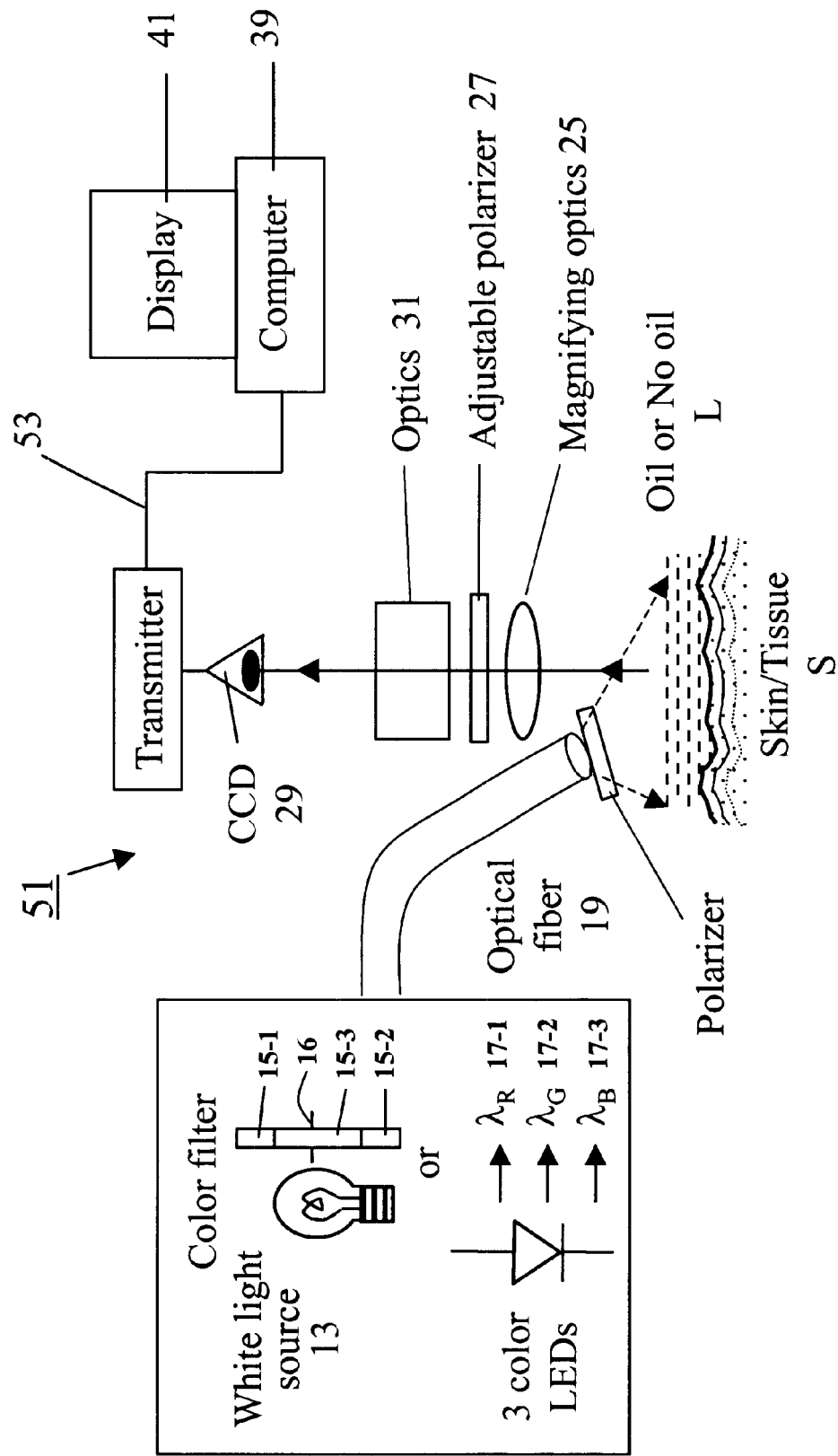
FIG. 3 is a schematic diagram of a second embodiment of an apparatus constructed according to the teachings of the present invention for use in examining objects.

Referring now to FIG. 3, there is shown a schematic diagram of a second embodiment of an apparatus constructed according to the teachings of the present invention for use in examining objects, said apparatus being represented generally by reference numeral 51.

Apparatus 51 is identical to apparatus 11, except that transmitter 35 and receiver 37 of apparatus 11 are replaced in apparatus 51 with a cable 53 coupled at one end to light detector 25 and at the other end to computer 39 for transmitting the output of detector 25 to computer 39.

Figure 4:
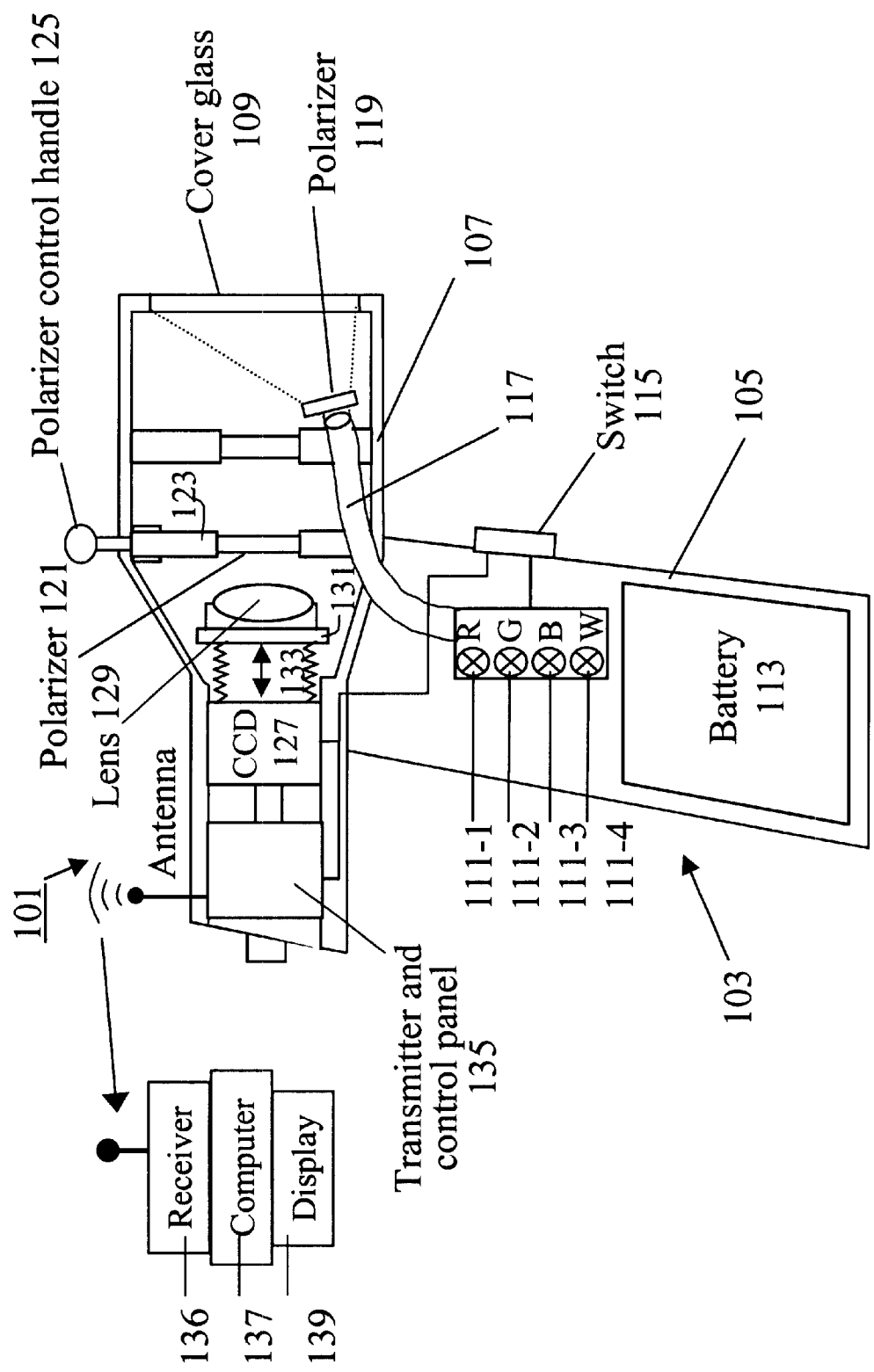
FIG. 4 is a schematic diagram of a third embodiment of an apparatus constructed according to the teachings of the present invention for use in examining objects.

Referring now to FIG. 4, there is shown a schematic diagram of a third embodiment of an apparatus constructed according to the teachings of the present invention for use in examining objects, said apparatus being represented generally by reference numeral 101.

Apparatus 101, which is functionally similar in many respects to apparatus 11, includes a hand-held housing 103. Housing 103 is gun-shaped and includes a handle portion 105 and a barrel portion 107. The front end of barrel portion 107 is open, and a glass cover 109 is mounted therein.

Apparatus 101 additionally comprises a red LED 111-1, a green LED 111-2, a blue LED 111-3, and a white LED 111-4, all of which are disposed within handle portion 105 of housing 103 and all of which are electrically connected to a battery 113 also disposed within handle portion 105 of housing 103. A manually-operable switch 115 for controlling actuation of each of LED's 111-1 through 111-4 is accessible on handle portion 105 of housing 103. An optical fiber 117 is disposed inside housing 103 and is used to transmit light from LED's 111 first through a first polarizer 119 disposed in barrel portion 107 of housing 103 and then through glass cover 109 to illuminate a desired object. Reflected or backscattered light from the object entering housing 103 through glass cover 109 is passed through a second polarizer 121 disposed in barrel portion 107 of housing 103. Polarizer 121 is mounted in a holder 123, and the orientation of polarizer 121 is manipulable by a handle 125 extending through housing 103 so that polarizer 121 can be used to select different polarization components of the light emitted from the illuminated object to permit surface or subsurface structures to be examined selectively.

Apparatus 101 further comprises imaging optics, said imaging optics being used to image the light passed through polarizer 121 onto a CCD detector 127. In the present embodiment, said imaging optics includes a lens 129 that is mounted on a barrel 131 with a screw 133 that permits lens 129 to be adjustably spaced relative to CCD detector 127. Detector 127 is coupled to a wireless transmitter 135 mounted in housing 103, transmitter 135 transmitting the output from detector 127 to a remotely located wireless receiver 136. Wireless receiver 136 is coupled to a computer 137, which then processes the output from detector 127. The processed output is then displayed on a display 139.

Apparatus 101 is particularly well-suited for mucosa and cervical examinations, as well as for skin examinations, as will hereinafter described below.

Figure 5:
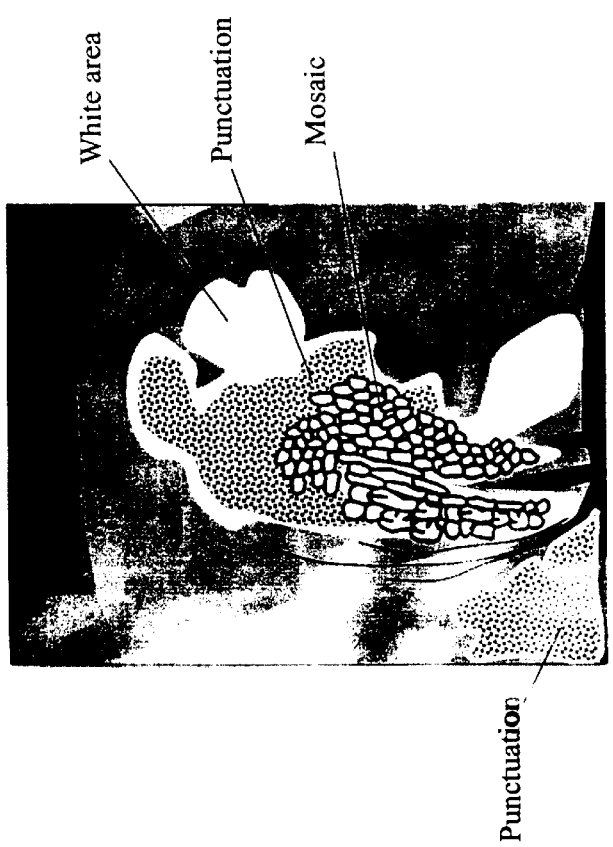
FIG. 5 is a schematic diagram of a cervical tissue sample following a washing with an acetic acid solution, showing different structure patterns.

As background, a colposcope is commonly used as an additional way to screen the cervix beyond a PAP smear. A colposcope consists of a stereoscopic binocular microscope with low magnification ~8 to 18×. It provides a center illuminator device mounted on an adjustable stand with wheels. A green filter is used between the cw white light source and tissue to accentuate the vascular pattern and color tone difference between normal and abnormal patterns. In colposcopy, the cervix is first cleansed with 3%–5% acetic acid solution to remove mucus and cellular debris. The acetic acid accentuates the difference between normal and abnormal patterns by hydrating the upper cellular layers. The colposcope is focused on the transformation zone, squamocolumnarjunction and four cervix quarters. Selected spots showing special features are collected for biopsies, such as areas denoted with enhanced punctuation, mosaicism and atypical vessels, and extra aceto-white (leukopakia) epithelium. These are CIN-2 and 3 zones requiring biopsy. White epithelium, mosaic structure, punctuation (vessel spots perpendicular to surface) give atyical CIN areas for biopsies (see FIG. 5). Atypical structures of vessels are often associated with invasive cancer requiring biopsy.

When using apparatus 101 for cervical examinations, one preferably cleanses the subject cervical tissue with 3%–5% acetic acid in the conventional manner prior to examination. Because a larger working distance (i.e., about 10–40 cm) is needed to view cervical tissue in vivo with magnification of 8 to 10×than would otherwise be needed for skin examinations, the spacing between lens 129 and detector 127 is different for cervical and skin applications. For example, with a 16 mm focal length camera video lens, a spacer of 5 mm gives a working distance of 23–26 mm (suitable for skin) whereas a spacer of 1 mm gives a working distance of 90–340 mm (suitable for cervix). Alternatively, with a 25 mm focal camera video lens, a 10 mm spacer gives a working distance of 41–45 mm (suitable for skin) whereas a spacer of 5 mm gives 81–118 mm and a spacer of 1 mm gives a working distance of 250–640 mm (suitable for cervix). By adjustably mounting lens 129 as in apparatus 101 so that different distances can be achieved between lens 129 and detector 127, the working distance can readily be adjusted as needed for different applications. The depolarized reflectance light from images of the cervix for uv, red, blue and green light is used to determine the various fingerprint structures of punctuation, mosaic and white areas for cancer.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. An apparatus suitable for use in examining skin, mucosa and cervical tissues for the purpose of detecting cancer and precancerous conditions therein, said apparatus comprising:

(a) first illuminating means for illuminating an object with polarized light of a first color;

(b) second illuminating means for illuminating an object with polarized light of a second color, said second color being different from said first color;

(c) a control coupled to each of said first illuminating means and said second illuminating means to permit selective actuation of said first illuminating means and said second illuminating means;

(d) a light detector for outputting an electrical signal in response to light incident thereonto;

(e) an adjustable polarizer positioned between said light detector and the illuminated object;

(f) optics for imaging light emitted from the illuminated object onto said light detector;

(g) a computer for processing the output from said light detector;

(h) means for transmitting the output from said light detector to said computer, wherein said means for transmitting the output from said light detector to said computer comprises a wireless transmitter coupled to said light detector and a wireless receiver coupled to said computer; and (i) a display for displaying the results of said processing by said computer.

2. The apparatus as claimed in claim 1 wherein said display is remotely located relative to said computer and is connected to said computer via modem.

3. An apparatus suitable for use in examining skin, mucosa and cervical tissues for the purpose of detecting cancer and precancerous conditions therein, said apparatus comprising:

(a) first illuminating means for illuminating an object with polarized light of a first color;

(b) second illuminating means for illuminating an object with polarized light of a second color, said second color being different from said first color;

(c) a control coupled to each of said first illuminating means and said second illuminating means to permit selective actuation of said first illuminating means and said second illuminating means;

(d) a light detector for outputting an electrical signal in response to light incident thereonto;

(e) an adjustable polarizer positioned between said light detector and the illuminated object, wherein said adjustable polarizer is alternately oriented to selectively transmit depolarized and polarized light emitted from the illuminated object and wherein said computer comprises means for forming an image based on the parallel and perpendicular polarization components of the light emitted from the illuminated object;

(f) optics for imaging light emitted from the illuminated object onto said light detector;

(g) a computer for processing the output from said light detector;

(h) means for transmitting the output from said light detector to said computer; and (i) a display for displaying the results of said processing by said computer.

4. An apparatus for use in examining an object, said apparatus comprising:

(a) a hand-held housing, said hand-held housing having an opening;

(b) first illuminating means, disposed inside said hand-held housing, for illuminating an object with light of a first color;

(c) second illuminating means, disposed inside said hand-held housing, for illuminating an object with light of a second color, said second color being different from said first color;

(d) a manually operable control switch coupled to each of said first illuminating means and said second illuminating means to permit selective actuation of said first illuminating means and said second illuminating means;

(e) an optical fiber disposed inside said hand-held housing and optically coupled at a first end to said first and second illuminating means and optically aligned at a second end with said opening;

(f) a first polarizer disposed inside said hand-held housing and optically aligned between said second end of said optical fiber and said opening of said hand-held housing;

(g) a light detector disposed inside said hand-held housing for outputting an electrical signal in response to light incident thereonto;

(h) a second polarizer disposed inside said hand-held housing, said second polarizer being positioned in front of and optically aligned with said light detector;

(i) optics for imaging onto said light detector light entering into said hand-held housing through said opening;

(j) a computer, disposed remotely relative to said hand-held housing, for processing the output from said light detector;

(k) a wireless receiver electrically coupled to said computer;

(l) a wireless transmitter electrically coupled to said light detector and mechanically coupled to said hand-held housing; and (m) a display coupled to said computer for displaying the results of said processing from said computer.

5. The apparatus as claimed in claim 4 further comprising a glass plate, said glass plate covering said opening in said hand-held housing.

6. The apparatus as claimed in claim 4 further comprising means extending through said hand-held housing for adjusting the orientation of said second polarizer.

7. The apparatus as claimed in claim 4 wherein said light detector is a CCD detector.

8. The apparatus as claimed in claim 4 wherein said first illuminating means comprises a first light-emitting diode of said first color and said second illuminating means comprises a second light-emitting diode of said second color.

9. The apparatus as claimed in claim 8 further comprising third illuminating means, disposed inside said hand-held housing, for illuminating an object with light of a third color, said third color being different from said first and second colors, said third illuminating means being coupled to said manually operable control switch to permit selective actuation of said first, second and third illuminating means, said third illuminating means being optically coupled to the first end of said optical fiber.

10. The apparatus as claimed in claim 9 wherein said third illuminating means comprises a third light-emitting diode of said third color.

11. The apparatus as claimed in claim 10 wherein said first illuminating means comprises a red light-emitting diode, said second illuminating means comprises a green light-emitting diode and said third illuminating means comprises a blue light-emitting diode.

12. The apparatus as claimed in claim 11 further comprising a white light-emitting diode disposed inside said hand-held housing, said white light-emitting diode being coupled to said manually operable control switch to permit selective actuation of said white, red, green and blue light-emitting diodes, said white light-emitting diode being optically coupled to the first end of said optical fiber.

13. The apparatus as claimed in claim 4 wherein said imaging optics comprises a lens disposed inside said hand-held housing and positioned in front of said light detector, said lens being adjustably spaced relative to said light detector for imaging.

14. The apparatus as claimed in claim 4 wherein said computer comprises means for creating an image of the illuminated object.

15. The apparatus as claimed in claim 4 wherein said computer comprises means for characterizing the carcinomatoid state of the object.

16. The apparatus as claimed in claim 4 wherein said display is remotely located relative to said computer and is connected to said computer via modem.

17. The apparatus as claimed in claim 4 wherein said second polarizer is oriented to selectively transmit depolarized light emitted from the illuminated object.

18. The apparatus as claimed in claim 4 wherein said second polarizer is alternately oriented to selectively transmit polarized and depolarized light emitted from the illuminated object and wherein said computer comprises means for forming an image based on the parallel and perpendicular polarization components of the light emitted from the illuminated object.

19. The apparatus as claimed in claim 4 wherein said apparatus is used to image cervical tissue.

20. The apparatus as claimed in claim 4 wherein said apparatus is used to image skin.

21. The apparatus as claimed in claim 4 wherein said apparatus is used to detect precancerous and cancerous states in skin, cervix and mucosa by structural analysis.

22. The apparatus as claimed in claim 4 wherein said apparatus is used to transfer images by telemedicine to be analyzed for cancer by an expert at a remote site.

23. The apparatus as claimed in claim 4 wherein an ABCD matrix and the blue veil are used to detect cancer, in particular, melanoma.

24. The apparatus as claimed in claim 4 wherein depolarized light in the red, blue and greens is used to get depth information.

25. The apparatus as claimed in claim 4 wherein the spatial (x,y) distribution of Kubelka-Munk flnction is used to form a KMF map of a tissue area to determine structural changes associated with cancer and precancer.

* * * * *